United States Patent [19]

Frey et al.

[11] Patent Number: 4,955,908
[45] Date of Patent: Sep. 11, 1990

[54] METALLIC INTERVERTEBRAL PROSTHESIS

[75] Inventors: Otto Frey, Winterthur; Rudolf Koch, Berlingen, both of Switzerland

[73] Assignee: Sulzer Brothers Limited, Winterthur, Switzerland

[21] Appl. No.: 203,950

[22] Filed: Jun. 8, 1988

[30] Foreign Application Priority Data

Jul. 9, 1987 [CH] Switzerland ............ 2605/87

[51] Int. Cl.$^5$ ............ A61F 5/04; A61F 2/30
[52] U.S. Cl. ............ 623/17; 128/69; 606/61
[58] Field of Search ............ 623/17; 128/69, 92 YM; 606/61

[56] References Cited

U.S. PATENT DOCUMENTS

| | | |
|---|---|---|
| 3,840,904 | 10/1974 | Tronzo ............ 623/23 |
| 3,867,728 | 2/1975 | Stubstad . |
| 4,349,921 | 9/1982 | Kuntz ............ 623/17 |
| 4,599,086 | 7/1986 | Doty ............ 623/17 |
| 4,714,469 | 12/1987 | Kenna ............ 623/17 |

FOREIGN PATENT DOCUMENTS

| | | |
|---|---|---|
| 0179695 | 4/1986 | European Pat. Off. . |
| 2263842 | 4/1974 | Fed. Rep. of Germany . |
| 2365873 | 8/1976 | Fed. Rep. of Germany . |
| 3637314 | 5/1988 | Fed. Rep. of Germany ........ 623/17 |
| 1107854 | 8/1984 | U.S.S.R. ............ 623/17 |

Primary Examiner—V. Millin
Attorney, Agent, or Firm—Kenyon & Kenyon

[57] ABSTRACT

The metallic intervertebral prosthesis is formed of a kidney-shaped body having fishplates extending upwardly and downwardly from the body. Each fishplate has an opening for passage of a bone screw in order to secure the prosthesis to and between adjacent vertebrae. The body is tapered conically from ventral to dorsal and may be fitted in place in the ventral direction. A metal wire mesh may be provided on opposed surfaces of the body for the ingrowth of tissue and ribs may be provided to enhance lateral stability.

10 Claims, 1 Drawing Sheet

METALLIC INTERVERTEBRAL PROSTHESIS

This invention relates to an intervertebral prosthesis. More particularly, this invention relates to a metallic intervertebral prosthesis for an arthrodesis.

As is known, for an arthrodesis of two lumbar vertebrae relative to each other, two different approaches have been customary. In one approach, bone splinters have been removed from another part of the body, for example, from the pelvis or the shin, and placed as a partial replacement of the damaged intervertebral disk between the two vertebrae from the ventral direction and secured with bone screws. However, it has been shown that securement of the two adjacent vertebrae is insufficient and does not have the requisite stability, especially shortly after implantation when the bone tissue of the Vertebrae has not yet become intergrown with the bone splinters.

In the other approach, two adjacent vertebrae have been secured relative to each other by cross plates which are firmly connected with the two vertebrae from the dorsal direction, for example by means of screws. However, experience has shown that the cross plates which are arranged relatively far from the intervertebral disks effect only an insufficient securement of the vertebrae in the dorsal region of the vertebrae, particularly in the case of a greater intervertebral disk damage or in the case of a complete replacement of an intervertebral disk. Also, the plates tend toward instabilities in the reciprocable stiffening of the vertebrae.

Various types of intervertebral prosthesis have also been known for implantation within a spinal column. For example, German OS 2365873 describes a skeletal type prosthesis which can be implanted in place of a vertebrae and secured in situ by means of screws to adjacent vertebrae. German OS 2263842 describes a composite disk like structure which is to be implanted between a pair of vertebrae to replace a damaged disk. However, the stability of such a prosthesis cannot be ensured since no means is provided for a primary fixation of the prosthesis in place. Published European patent application 0179695 describes a prosthesis which is intended to replace a damaged disk and which is constructed of a peripheral ring with a multi-apertured insert. However, such a prosthesis is relatively cumbersome to use and does not provide for a primary fixation of the prosthesis in situ. U.S. Pat. No. 3,867,728 describes a prosthesis for spinal repair which is made of a core element of elastic polymer and an outer covering of pore-like material to provide for tissue ingrowth. However, the securement of such a prosthesis in place cannot be readily obtained and the prosthesis does not have the required stability for primary fixation.

Accordingly, it is an object of the invention to provide an implantable and securable intervertebral prosthesis Which can be mounted in place with relatively little operative expenditure.

It is another object of the invention to provide an intervertebral prosthesis which is capable of a secure and stable stiffening of an arthrodesis.

It is another object of the invention to provide an intervertebral prosthesis of relatively simple construction.

Briefly, the invention provides an intervertebral prosthesis for an arthrodesis which is comprised of a disk-like body for fitting between a pair of vertebrae and have a plurality of fishplates extending from opposite sides of the body. In addition, each fishplate is provided with an opening for passage of a bone screw into an adjacent vertebrae.

The prosthesis is distinguished by great simplicity as the prosthesis consists solely of a plate for replacing an intervertebral disk. The primary securement of the prosthesis takes place by means of bone screws which can be screwed into the prosthesis body from the ventral direction after the prosthesis body has been slid from the ventral direction into the interspace between the vertebrae. In this respect, sliding in of the prosthesis body occurs after the interspace has been cleared of the destroyed or damaged intervertebral disk.

In order to adapt the prosthesis body to the anatomical parameters, the thickness of the body tapers conically from ventral to dorsal. In addition, the prosthesis body may be kidney shaped.

For long term seCurement, the disk surfaces of the prosthesis body are provided with a structure for an ingrowth of bone tissue. In particular, the structure may be a metal wire mesh of at least one layer thickness. Such a mesh may be attached on the disk surfaces of the prosthesis bodY by spot welding of the mesh to distributed points over the area of the disk.

In order to increase the lateral stability of the prosthesis body, a raised rib is provided on each of the opposite surfaces. This rib may be of chevron shape and may have a cross section of cylindrical segment shape.

Suitable materials for the prosthesis body may be any metal or metal alloy used in implantation technology. Preferably, the body is made of titanium or titanium alloys.

These and other objects and advantages of the invention will become more apparent from the following detailed description taken in conjunction with the accompanying drawings wherein.

Figure 1:
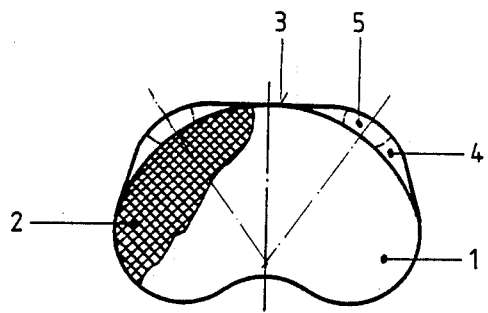
FIG. 1 illustrates a plan view of a prosthesis constructed in accordance with the invention.
Figure 2:
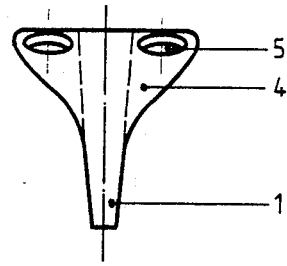
FIG. 2 illustrates a side view of the prosthesis of FIG. 1.

Referring to FIGS. 1 and 2, the intervertebral prosthesis is made of any suitable metal and includes a solid disk-like body 1 for fitting between a pair Of vertebrae. As shown in FIG. 1, the body 1 is curved convex ventrally and concave dorsally to have a kidney shape. Also, as indicated in FIG. 2, the body 1 having a thickness less than the height thereof tapers conically from Ventral to dorsal.

As indicated in FIG. 1, a structure 2, for example of a metal wire mesh of single layer is provided on opposite surfaces of the body 1 for the ingrowth of tissue. The structure 2 is fastened through spot weldings which are distributed over the kidney-shaped disk surfaces.

The prosthesis is also provided with a plurality of fishplates 4 which extend from opposite sides and which are disposed symmetrically to the center plane of the body 1. As indicated in FIG. 2, the fishplates 4 extend upward and downward from the disk body 1 and each is provided with an opening for passage of a bone screw (not shown). As indicated in FIG. 1, the fishplates 4 are provided on the ventral convex edge 3 of the body 1 and each is provided with a bore or opening 5 to receive a bone screw (not shown). The bores 5 are designed as part of a cup-shaped part in order to facilitate the lining of the screws in a line.

Figure 3:
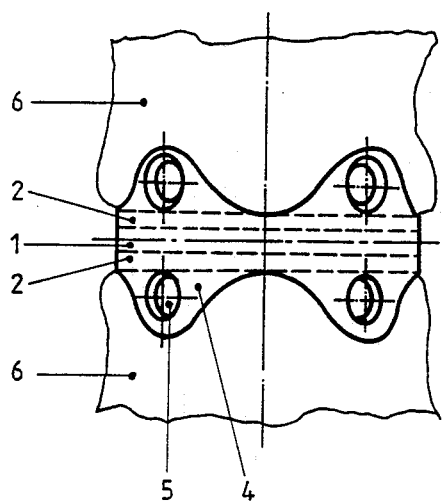
FIG. 3 illustrates a ventral view of the prosthesis of FIG. 1 in situ.

Referring to FIG. 3, the prosthesis body 1 is inserted between a pair of vertebrae 6 from ventral to dorsal. In addition, bone screws (not shown) are passed through the openings 5 into the respective vertebrae 6 for primary securement of the prosthesis body 1. As indicated, the fishplates 4 cling intimately to each vertebrae 6.

Figure 4:
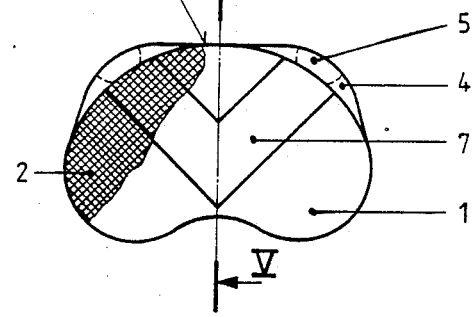
FIG. 4 illustrates a modified prosthesis having a structure for the ingrowth of tissue thereon.
Figure 5:
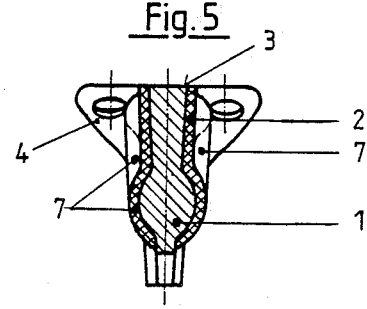
FIG. 5 illustrates a view taken on line V—V of FIG. 4.

Referring to FIGS. 4 and 5, wherein like reference characters indicate like parts as above as described in copending application Ser. No. 204,020, filed June 8, 1988, a raised rib 7 may be formed on each of the two opposite surfaces of the prosthesis body 1 in order to enhance laterally stability. As indicated in FIG. 4, the rib 7 is of chevron-shape. In addition, as indicated in FIG. 5, the rib 7 has a cross section of cylindrical segment shape.

The invention thus provides a relatively simple intervertebral prosthesis which can be readily inserted and secured in place. Further, the prosthesis ensures a stable stiffening (arthrodesis) of two vertebrae relative to each other immediately after implantation by being screwed to the vertebrae as well as over the long term through bone tissue growing into and on the prosthesis.

What is claimed is:

1. A metallic intervertebral prosthesis for an arthodesis comprising a disk-like body having a width less than the height thereof and tapering conically from the ventral to dorsal for fitting between a pair of vertebrae to replace an intervertebral disk and having a plurality of fishplates extending from opposite sides thereof, each said fishplate having an opening for passage of a bone screw into an adjacent vertebrae.

2. An intervertebral prosthesis as set forth in claim 1 which further comprises a structure disposed on opposite surfaces of said body for an ingrowth of bone tissue.

3. An intervertebral prosthesis as set forth in claim 1 wherein said body has a raised rib on each of two opposite surfaces to enhance lateral stability thereof.

4. An intervertebral prosthesis as set forth in claim 3 wherein said rib has a cross-section of cylindrical segment shape.

5. An intervertebral prosthesis as set forth in claim 4 wherein said rib is of chevron-shape.

6. An intervertebral prosthesis for an arthodesis comprising a solid disk-like body having a less width than the height thereof and tapering conically from ventral to dorsal for fitting between a pair of vertebrae to replace an intervertebral disk, said body having a plurality of integral fishplates extending perpendicularly from a ventral side thereof, each fishplate having an opening for passage of a bone screw into an adjacent vertebrae.

7. An intervertebral prosthesis as set forth in claim 6 which further comprises a structure disposed on opposite surfaces of said body for an ingrowth of bone tissue.

8. An intervertebral prosthesis as set forth in claim 7 wherein said body has a raised rib on each of two opposite surfaces to enhance lateral stability thereof.

9. A metallic intervertebral prosthesis for an arthodesis comprising a disk-like body of kidney shape having a width less than the height thereof and tapering conically from the ventral to dorsal for fitting between a pair of vertebrae to replace an intervertebral disk and having a plurality of fishplates extending from opposite sides thereof, each side fishplate having an opening for passage of a bone screw into an adjacent vertebrae.

10. A metallic intervertebral prosthesis for an arthodesis comprising a disk-like body having a width less than the height thereof and tapering conically from the ventral to dorsal for fitting between a pair of vertebrae to replace an intervertebral disk and having a plurality of fishplates extending from opposite sides thereof, each said fishplate having an opening for passage of a bone screw into an adjacent vertebrae, and a wire mesh disposed on opposite surfaces of said body for an ingrowth of bone tissue.

* * * * *